US008439971B2

(12) United States Patent
Reuter et al.

(10) Patent No.: US 8,439,971 B2
(45) Date of Patent: *May 14, 2013

(54) ADJUSTABLE HEIGHT FOCAL TISSUE DEFLECTOR

(75) Inventors: David Reuter, Bothell, WA (US); Mark Mathis, Fremont, CA (US); Greg Nieminen, Bothell, WA (US); Cruz Beeson, Sacramento, CA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 371 days.

This patent is subject to a terminal disclaimer.

(21) Appl. No.: 12/642,525

(22) Filed: Dec. 18, 2009

(65) Prior Publication Data
US 2010/0100175 A1   Apr. 22, 2010

Related U.S. Application Data

(63) Continuation of application No. 10/861,782, filed on Jun. 3, 2004, now Pat. No. 7,635,387, which is a continuation-in-part of application No. 10/003,910, filed on Nov. 1, 2001, now Pat. No. 6,949,122, and a continuation-in-part of application No. 10/429,204, filed on May 2, 2003, now Pat. No. 7,311,729, which is a continuation-in-part of application No. 10/142,637, filed on May 8, 2002, now Pat. No. 6,824, 562.

(60) Provisional application No. 60/476,666, filed on Jun. 5, 2003.

(51) Int. Cl.
*A61F 2/24* (2006.01)

(52) U.S. Cl.
USPC .......................................................... 623/2.37

(58) Field of Classification Search ........... 623/1.1–2.42
See application file for complete search history.

(56) References Cited

U.S. PATENT DOCUMENTS

| 3,620,212 A | 11/1971 | Fannon, Jr. et al. |
| 3,786,806 A | 1/1974 | Johnson et al. |

(Continued)

FOREIGN PATENT DOCUMENTS

| EP | 0893133 | 1/1999 |
| EP | 0903110 A1 | 3/1999 |

(Continued)

OTHER PUBLICATIONS

Nieminen et al.; U.S. Appl. No. 12/907,907 entitled "Tissue Shaping Device," filed Oct. 19, 2010.

(Continued)

*Primary Examiner* — Scott Getzow
(74) *Attorney, Agent, or Firm* — Shay Glenn LLP

(57) ABSTRACT

A tissue shaping device adapted to reshape target tissue adjacent to a lumen. In some embodiments, the device includes an expandable and contractable anchor, with the anchor having an adjustable height anchoring portion adapted to engage a wall of the lumen in at least first and second anchor heights, the anchoring portion being further adapted to be changed from the first anchor height to the second anchor height by a substantially proximally or a substantially distally directed actuation force. The invention is also a tissue shaping system including a tissue shaping device and a tool for adjusting the height of an anchor of the device. The invention also includes methods of using such tissue shaping devices and systems.

28 Claims, 6 Drawing Sheets

U.S. PATENT DOCUMENTS

| | | | |
|---|---|---|---|
| 3,890,977 A | 6/1975 | Wilson | |
| 3,974,526 A | 8/1976 | Dardik et al. | |
| 3,995,623 A | 12/1976 | Black et al. | |
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,099,838 A | 3/1992 | Bardy | |
| 5,104,404 A | 4/1992 | Wolff | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,433,727 A | 7/1995 | Sideris | |
| 5,441,515 A | 8/1995 | Khosravi et al. | |
| 5,449,373 A | 9/1995 | Pinchasik et al. | |
| 5,454,365 A | 10/1995 | Bonutti | |
| 5,458,615 A | 10/1995 | Klemm et al. | |
| 5,474,557 A | 12/1995 | Mai | |
| 5,507,295 A | 4/1996 | Skidmore | |
| 5,507,802 A | 4/1996 | Imran | |
| 5,514,161 A | 5/1996 | Limousin | |
| 5,554,177 A | 9/1996 | Kieval et al. | |
| 5,562,698 A | 10/1996 | Parker | |
| 5,575,818 A | 11/1996 | Pinchuk | |
| 5,584,867 A | 12/1996 | Limousin et al. | |
| 5,601,600 A | 2/1997 | Ton | |
| 5,617,854 A | 4/1997 | Munsif | |
| 5,662,703 A | 9/1997 | Yurek et al. | |
| 5,676,671 A | 10/1997 | Inoue | |
| 5,733,325 A | 3/1998 | Robinson et al. | |
| 5,741,297 A | 4/1998 | Simon | |
| 5,752,969 A | 5/1998 | Cunci et al. | |
| 5,800,519 A | 9/1998 | Sandock | |
| 5,824,071 A | 10/1998 | Nelson et al. | |
| 5,836,882 A | 11/1998 | Frazin | |
| 5,871,501 A | 2/1999 | Leschinsky et al. | |
| 5,891,193 A | 4/1999 | Robinson et al. | |
| 5,895,391 A | 4/1999 | Farnholtz | |
| 5,899,882 A | 5/1999 | Waksman et al. | |
| 5,908,404 A | 6/1999 | Elliott | |
| 5,928,258 A | 7/1999 | Khan et al. | |
| 5,935,161 A | 8/1999 | Robinson et al. | |
| 5,954,761 A | 9/1999 | Machek et al. | |
| 5,961,545 A | 10/1999 | Lentz et al. | |
| 5,978,705 A | 11/1999 | KenKnight et al. | |
| 5,984,944 A | 11/1999 | Forber | |
| 6,007,519 A | 12/1999 | Rosselli | |
| 6,015,402 A | 1/2000 | Sahota | |
| 6,022,371 A | 2/2000 | Killion | |
| 6,027,517 A | 2/2000 | Crocker et al. | |
| 6,045,497 A | 4/2000 | Schweich, Jr. et al. | |
| 6,053,900 A | 4/2000 | Brown et al. | |
| 6,056,775 A | 5/2000 | Borghi et al. | |
| 6,077,295 A | 6/2000 | Limon et al. | |
| 6,077,297 A | 6/2000 | Robinson et al. | |
| 6,080,182 A | 6/2000 | Shaw et al. | |
| 6,086,611 A | 7/2000 | Duffy et al. | |
| 6,096,064 A | 8/2000 | Routh | |
| 6,099,549 A | 8/2000 | Bosma et al. | |
| 6,099,552 A | 8/2000 | Adams | |
| 6,129,755 A | 10/2000 | Mathis et al. | |
| 6,162,168 A | 12/2000 | Schweich, Jr. et al. | |
| 6,171,320 B1 | 1/2001 | Monassevitch | |
| 6,183,512 B1 | 2/2001 | Howanec et al. | |
| 6,190,406 B1 | 2/2001 | Duerig et al. | |
| 6,200,336 B1 | 3/2001 | Pavcnik et al. | |
| 6,210,432 B1 | 4/2001 | Solem et al. | |
| 6,228,098 B1 | 5/2001 | Kayan et al. | |
| 6,241,757 B1 | 6/2001 | An et al. | |
| 6,254,628 B1 | 7/2001 | Wallace et al. | |
| 6,267,783 B1 | 7/2001 | Letendre et al. | |
| 6,275,730 B1 | 8/2001 | KenKnight et al. | |
| 6,306,141 B1 | 10/2001 | Jervis | |
| 6,312,446 B1 | 11/2001 | Huebsch et al. | |
| 6,334,864 B1 | 1/2002 | Amplatz et al. | |
| 6,342,067 B1 | 1/2002 | Mathis et al. | |
| 6,345,198 B1 | 2/2002 | Mouchawar et al. | |
| 6,352,553 B1 | 3/2002 | van der Burg et al. | |
| 6,352,561 B1 | 3/2002 | Leopold et al. | |
| 6,358,195 B1 | 3/2002 | Green et al. | |
| 6,395,017 B1 | 5/2002 | Dwyer et al. | |
| 6,402,781 B1 | 6/2002 | Langberg et al. | |
| 6,419,696 B1 | 7/2002 | Ortiz et al. | |
| 6,442,427 B1 | 8/2002 | Boute et al. | |
| 6,464,720 B2 | 10/2002 | Boatman et al. | |
| 6,478,776 B1 | 11/2002 | Rosenman et al. | |
| 6,503,271 B2 | 1/2003 | Duerig et al. | |
| 6,537,314 B2 * | 3/2003 | Langberg et al. | 623/2.36 |
| 6,556,873 B1 | 4/2003 | Smits | |
| 6,562,066 B1 | 5/2003 | Martin | |
| 6,562,067 B2 | 5/2003 | Mathis | |
| 6,569,198 B1 | 5/2003 | Wilson et al. | |
| 6,589,208 B2 | 7/2003 | Ewers et al. | |
| 6,599,314 B2 | 7/2003 | Mathis | |
| 6,602,288 B1 | 8/2003 | Cosgrove et al. | |
| 6,602,289 B1 | 8/2003 | Colvin et al. | |
| 6,623,521 B2 | 9/2003 | Steinke et al. | |
| 6,626,899 B2 | 9/2003 | Houser et al. | |
| 6,629,534 B1 | 10/2003 | St. Goar et al. | |
| 6,629,994 B2 | 10/2003 | Gomez et al. | |
| 6,643,546 B2 | 11/2003 | Mathis et al. | |
| 6,648,881 B2 | 11/2003 | KenKnight et al. | |
| 6,652,538 B2 | 11/2003 | Kayan et al. | |
| 6,656,221 B2 | 12/2003 | Taylor et al. | |
| 6,676,702 B2 | 1/2004 | Mathis | |
| 6,689,164 B1 | 2/2004 | Seguin | |
| 6,709,425 B2 | 3/2004 | Gambale et al. | |
| 6,716,158 B2 | 4/2004 | Raman et al. | |
| 6,718,985 B2 | 4/2004 | Hlavka et al. | |
| 6,721,598 B1 | 4/2004 | Helland et al. | |
| 6,723,038 B1 | 4/2004 | Schroeder et al. | |
| 6,733,521 B2 | 5/2004 | Chobotov et al. | |
| 6,743,219 B1 | 6/2004 | Dwyer et al. | |
| 6,764,510 B2 | 7/2004 | Vidlund et al. | |
| 6,773,446 B1 | 8/2004 | Dwyer et al. | |
| 6,776,784 B2 | 8/2004 | Ginn | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,798,231 B2 | 9/2004 | Iwasaki et al. | |
| 6,800,090 B2 | 10/2004 | Alferness et al. | |
| 6,805,128 B1 | 10/2004 | Pless et al. | |
| 6,810,882 B2 | 11/2004 | Langberg et al. | |
| 6,821,297 B2 | 11/2004 | Snyders | |
| 6,824,562 B2 | 11/2004 | Mathis et al. | |
| 6,827,690 B2 | 12/2004 | Bardy | |
| 6,881,220 B2 | 4/2005 | Edwin et al. | |
| 6,899,734 B2 | 5/2005 | Castro et al. | |
| 6,908,478 B2 | 6/2005 | Alferness et al. | |
| 6,908,482 B2 | 6/2005 | McCarthy et al. | |
| 6,935,404 B2 | 8/2005 | Duerig et al. | |
| 6,949,122 B2 | 9/2005 | Adams et al. | |
| 6,955,689 B2 | 10/2005 | Ryan et al. | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 6,976,995 B2 | 12/2005 | Mathis et al. | |
| 7,004,958 B2 | 2/2006 | Adams et al. | |
| 7,152,605 B2 | 12/2006 | Khairkhahan et al. | |
| 7,175,653 B2 | 2/2007 | Gaber | |
| 7,179,282 B2 | 2/2007 | Alferness et al. | |
| 7,311,729 B2 | 12/2007 | Mathis et al. | |
| 7,316,708 B2 | 1/2008 | Gordon et al. | |
| 7,364,588 B2 | 4/2008 | Mathis et al. | |
| 7,591,826 B2 | 9/2009 | Alferness et al. | |
| 7,955,384 B2 * | 6/2011 | Rafiee et al. | 623/2.11 |
| 2001/0018611 A1 | 8/2001 | Solem et al. | |
| 2001/0041899 A1 | 11/2001 | Foster | |
| 2001/0044568 A1 | 11/2001 | Langberg et al. | |
| 2001/0049558 A1 | 12/2001 | Liddicoat et al. | |
| 2002/0016628 A1 | 2/2002 | Langberg et al. | |
| 2002/0042621 A1 | 4/2002 | Liddicoat et al. | |
| 2002/0042651 A1 | 4/2002 | Liddicoat et al. | |

| Publication No. | Date | Inventor |
|---|---|---|
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2003/0135267 A1 | 7/2003 | Solem et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg et al. |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0249452 A1 | 12/2004 | Adams et al. |
| 2004/0260342 A1 | 12/2004 | Vargas et al. |
| 2004/0260384 A1 | 12/2004 | Allen |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0060030 A1 | 3/2005 | Lashinski et al. |
| 2005/0085903 A1 | 4/2005 | Lau |
| 2005/0096666 A1 | 5/2005 | Gordon et al. |
| 2005/0096740 A1 | 5/2005 | Langberg et al. |
| 2005/0107810 A1 | 5/2005 | Morales et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0177228 A1 | 8/2005 | Solem et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0222678 A1 | 10/2005 | Lashinski et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0191121 A1 | 8/2006 | Gordon et al. |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |
| 2007/0135912 A1 | 6/2007 | Mathis |
| 2007/0239270 A1 | 10/2007 | Mathis et al. |
| 2008/0015407 A1 | 1/2008 | Mathis et al. |
| 2008/0015679 A1 | 1/2008 | Mathis et al. |
| 2008/0015680 A1 | 1/2008 | Mathis et al. |
| 2008/0071364 A1 | 3/2008 | Kaye et al. |
| 2008/0097594 A1 | 4/2008 | Mathis et al. |
| 2008/0109059 A1 | 5/2008 | Gordon et al. |
| 2008/0140191 A1 | 6/2008 | Mathis et al. |
| 2008/0319542 A1 | 12/2008 | Nieminen et al. |
| 2010/0031793 A1 | 2/2010 | Hayner et al. |
| 2012/0197389 A1 | 8/2012 | Alferness et al. |

FOREIGN PATENT DOCUMENTS

| | | |
|---|---|---|
| EP | 0968688 A1 | 1/2000 |
| EP | 1050274 A1 | 11/2000 |
| EP | 1095634 A2 | 5/2001 |
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| SE | 9902455 | 12/2000 |
| WO | WO 98/56435 A1 | 12/1998 |
| WO | WO 00/44313 A1 | 8/2000 |
| WO | WO 00/60995 A2 | 10/2000 |
| WO | WO 00/74603 A1 | 12/2000 |
| WO | WO 01/00111 A1 | 1/2001 |
| WO | WO 01/19292 A1 | 3/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/037171 A2 | 5/2003 |
| WO | WO 03/049647 A1 | 6/2003 |
| WO | WO 03/049648 A2 | 6/2003 |
| WO | WO 03/055417 A1 | 7/2003 |
| WO | WO 03/059198 A2 | 7/2003 |
| WO | WO 03/063735 A2 | 8/2003 |
| WO | WO 2004/045463 A2 | 6/2004 |
| WO | WO 2004/084746 | 10/2004 |
| WO | WO 2005/046531 | 5/2005 |
| WO | WO 2005058206 A1 | 6/2005 |

OTHER PUBLICATIONS

Gordon et al.; U.S. Appl. No. 12/952,057 entitled "Percutaneous Mitral Valve Annuloplasty Delivery System," filed Nov. 22, 2010.

Mathis et al.; U.S. Appl. No. 13/004,239 entitled "Device and Method for Modifying the Shape of a Body Organ," filed Jan. 11, 2011.

Mathis, Mark L.; U.S. Appl. No. 12/838,189 entitled "Mitral Valve Device Using Conditioned Shape Memory Alloy," filed Jul. 16, 2010.

Hayner et al.; U.S. Appl. No. 13/220,444 entitled "Catheter cutting tool," filed Aug. 29, 2011.

Pelton et al. Medical uses of nitinol; Material Science Forum; vols. 327-328; pp. 63-70; 2000.

El-Maasarany et al.; The coronary sinus conduit function: Anatomical study (relationship to adjacent structures); http://europace.oxfordjournals.org/cge/content/full/7/5/475. (accessed Sep. 9, 2008).

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. 1997; 96(6): 1893-1898.

Pijls et al.; Measurement of fractional flow reserve to assess the functional severity of coronary-artery stenoses; The New England J. of Med.; vol. 334; No. 26; pp. 1703-1708; Jun. 27, 1996.

Pai, Suresh; U.S. Appl. No. 60/329,694 entitled "Percutaneous cardiac support structures and deployment means," filed Oct. 16, 2001.

Yamanouchi, et al.; Activation Mapping from the coronary sinus may be limited by anatomic variations; vol. 21 pp. 2522-2526; Nov. 1998.

Alferness et al.; U.S. Appl. No. 12/719,758 entitled "Device and Method for Modifying the Shape of a Body Organ," filed Mar. 8, 2010.

Mathis, Mark L.; U.S. Appl. No. 13/359,307 entitled "Devices and Methods for Reducing Mitral Valve Regurgitation," filed Jan. 26, 2012.

* cited by examiner

ADJUSTABLE HEIGHT FOCAL TISSUE DEFLECTOR

CROSS-REFERENCE TO RELATED APPLICATIONS

This application is a continuation of U.S. application Ser. No. 10/861,782, filed Jun. 3, 2004, now U.S. Pat. No. 7,635,387; which claims the benefit of U.S. Provisional Appln. No. 60/476,666, filed Jun. 5, 2003. Said U.S. application Ser. No. 10/861,782 is also a continuation-in-part of U.S. application Ser. No. 10/003,910, filed Nov. 1, 2001, now U.S. Pat. No. 6,949,122; and is a continuation-in-part of U.S. application Ser. No. 10/429,204, filed May 2, 2003, now U.S. Pat. No. 7,311,729; which, in turn, is a continuation-in-part of U.S. application Ser. No. 10/142,637, filed May 8, 2002, now U.S. Pat. No. 6,824,562. All of these applications are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

U.S. application Ser. No. 10/003,910, "Focused Compression Mitral Valve Device and Method;" U.S. application Ser. No. 10/142,637, "Body Lumen Device Anchor, Device and Assembly;" U.S. application Ser. No. 10/331,143, "System and Method to Effect the Mitral Valve Annulus of a Heart;" and U.S. application Ser. No. 10/429,172, "Device and Method for Modifying the Shape of a Body Organ," filed May 2, 2003; which are assigned to Cardiac Dimensions Inc., (the assignee of the present invention) and are herein incorporated by reference, disclose a variety of tissue deflecting mechanisms. In one application, the deflecting mechanisms engage a vessel wall in a coronary sinus and great cardiac vein to aid the closure of a regurgitating mitral valve. These devices generally include a connector (such as a cable or support wire) extending between a proximal anchor and a distal anchor engaging the lumen wall. The devices can be deployed to reshape the coronary sinus and the adjacent mitral valve annulus.

The purpose of a support device in a lumen such as a vein or artery is to reshape a particular tissue area adjacent to the lumen. In order to be minimally invasive, the reshaping should be limited to the target tissue, such as the mitral valve annulus, and any reshaping of other tissue adjacent to the lumen should be minimized or avoided. For example, to treat mitral valve regurgitation, the device is placed in the coronary sinus to reshape the mitral valve annulus. Care should be taken to minimize the reshaping of other adjacent tissue, such as nearby arteries. See, e.g., the following applications (the disclosures of which are incorporated herein by reference): U.S. application Ser. No. 09/855,945, "Mitral Valve Therapy Device, System and Method" (published Nov. 14, 2002, as US 2002/0169504 A1); U.S. application Ser. No. 09/855,946, "Mitral Valve Therapy Assembly and Method" (published Nov. 14, 2002, as US 2002/0169502 A1). It is also advisable to monitor cardiac perfusion during and after such mitral valve regurgitation therapy. See, e.g., U.S. application Ser. No. 10/366,585, "Method of Implanting a Mitral Valve Therapy Device," the disclosure of which is incorporated herein by reference.

Tissue shaping devices that apply force to a localized, discrete portion of the vessel wall surrounding a lumen have been described. See, e.g., U.S. application Ser. No. 10/003,910, "Focused Compression Mitral Valve Device and Method," which describes the use of such devices disposed in the coronary sinus to treat mitral valve regurgitation. Other therapies deploy one or more rigid devices in the lumen to change the shape of the lumen and adjacent tissue. See, e.g., Lashinski et al. U.S. application Ser. No. 10/066,302 (published as US 2002/0151961 A1); Taylor et al. U.S. application Ser. No. 10/068,264 (published as US 2002/0183835 A1); Liddicoat et al. U.S. application Ser. No. 10/112,354 (published as US 2002/0183838 A1); the disclosures of which are incorporated herein by reference. Still other tissue shaping devices utilize an "anchor and cinch" method to modify tissue adjacent a lumen, i.e., by anchoring a distal anchor, placing a proximally-directed force on a connector extending proximally from the distal anchor, and anchoring a proximal anchor to maintain the configuration.

SUMMARY OF THE INVENTION

The present invention is a mechanism for selectively controlling the anchor height of an anchor to be used as a proximal anchor, a distal anchor, or a focal tissue deflector. As with other tissue shaping devices, one particular application is the treatment of mitral valve regurgitation by deploying a device in the coronary sinus to reshape the mitral valve annulus.

One aspect of the invention provides a tissue shaping device adapted to reshape target tissue adjacent to a lumen. In some embodiments, the device has an expandable and contractable anchor. The anchor in these embodiments has an adjustable height anchoring portion adapted to engage a wall of the lumen in at least first and second anchor heights, the anchoring portion being further adapted to be changed from the first anchor height to the second anchor height by a substantially proximally or a substantially distally directed actuation force. In some embodiments the adjustable height anchoring portion includes a bent wire portion (formed, e.g., in a FIG. 8 configuration) adapted to change its shape in response to the actuation force. The anchor may also include a plurality of locks each adapted to lock the anchoring portion in an anchoring height, and the bent wire portion may include a locking portion adapted to cooperate with each lock to maintain the bent wire portion's shape.

In some embodiments the tissue shaping device has an anchor height adjustment tool interface. In some embodiments the device has a second anchor and a connector disposed between the first and second anchor.

The device may be part of a system including an anchor height adjustment mechanism adapted to register the adjustable height anchoring portion in a plurality of predetermined anchor heights. In some embodiments the anchor height adjustment mechanism may include locks locking the adjustable height anchoring portion in each of the predetermined anchor heights. In some embodiments the anchor height adjustment mechanism may include a plurality of points of connection between the adjustable height anchoring portion and a base portion of the anchor. For example, where the adjustable height anchoring portion includes a bent wire portion and the anchor's base portion includes a tube, the anchor height adjustment mechanism may include slots formed in the tube and shaped to receive at least a portion of the anchor's bent wire portion. As another example, the anchor height adjustment mechanism may include shape changeable locks adapted to cooperate with a locking portion of the bent wire portion.

Another aspect of the invention is a tissue shaping system including an anchor height adjustment tool; and a tissue shaping device adapted to reshape target tissue adjacent to a lumen. In this aspect of the invention, the tissue shaping device includes an expandable and contractable anchor, with the anchor including an adjustable height anchoring portion adapted to engage a wall of the lumen in at least first and second anchor heights; and a tool interface adapted to receive a proximally or distally directed actuation force from the anchor height adjustment tool to change the adjustable height anchoring portion from the first anchor height to the second anchor height. In some embodiments the adjustable height anchoring portion includes a bent wire portion adapted to change its shape in response to the actuation force. The anchor may also include a plurality of locks each adapted to lock the anchoring portion in an anchoring height, and the bent wire portion may include a locking portion adapted to cooperate with each lock to maintain the bent wire portion's shape. In some embodiments the device has a second anchor and a connector disposed between the first and second anchor.

In some embodiments the tissue shaping device the tool interface is part of an anchor height adjustment mechanism, the anchor height adjustment mechanism being adapted to register the adjustable height anchoring portion in a plurality of predetermined anchor heights. The anchor height adjustment mechanism may have locks locking the adjustable height anchoring portion in each of the predetermined anchor heights. In embodiments in which the device's anchor has a base portion, the anchor height adjustment mechanism may have a plurality of points of connection between the adjustable height anchoring portion and the base portion.

Yet another aspect of the invention is a method of shaping target tissue adjacent to a lumen. In some embodiments the method includes the steps of delivering a tissue shaping device comprising an expandable and contractable anchor to a site in the lumen adjacent the target tissue; and applying a substantially distally or a substantially proximally directed actuation force on the anchor to change anchor height from a first lockable height to a second lockable height. For example, a substantially distally directed force may be used to increase anchor height, and a substantially proximally directed force may be used to decrease anchor height.

The anchor may have a height adjustment tool interface, in which case the applying step may include the step of engaging an anchor height adjustment tool with the height adjustment tool interface. The method may also include the step of unlocking the anchor from the first anchor height and locking the anchor in the second anchor height. The step of locking or unlocking the anchor may include the step of changing a shape of an anchor lock.

In some embodiments in which the anchor has an anchoring portion adapted to engage a wall of the lumen, the steps of locking and/or unlocking may include the step of changing a shape of at least a portion of the anchor.

Other aspects of the invention will be apparent from the following detailed description.

DETAILED DESCRIPTION OF THE INVENTION

Figure 1:
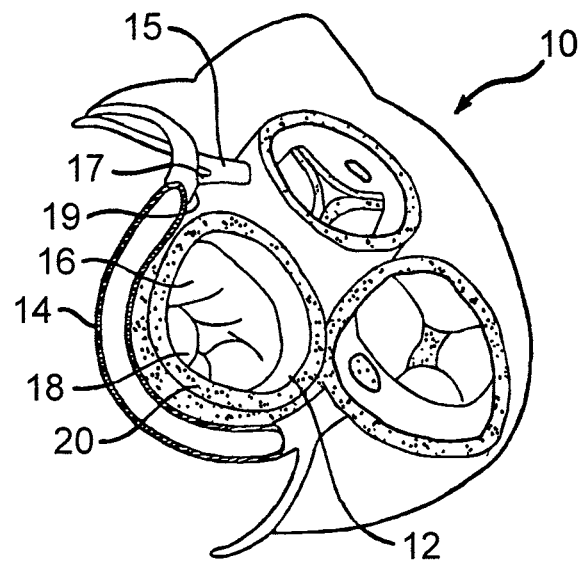
FIG. 1 is a superior view of a human heart with the atria removed.

FIG. 1 is a superior view of a human heart 10 with the atria removed to expose the mitral valve 12, the coronary sinus 14, the coronary artery 15, and the circumflex artery 17 of the heart 10. As used herein, "coronary sinus" includes the venous system associated with the coronary sinus including the great cardiac vein.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venous system of the heart and extends along the AV groove between the left atrium and the left ventricle. This places the coronary sinus essentially within the same plane as the mitral valve annulus making the coronary sinus available for placement of a mitral valve therapy device, such as described below.

Figure 2:
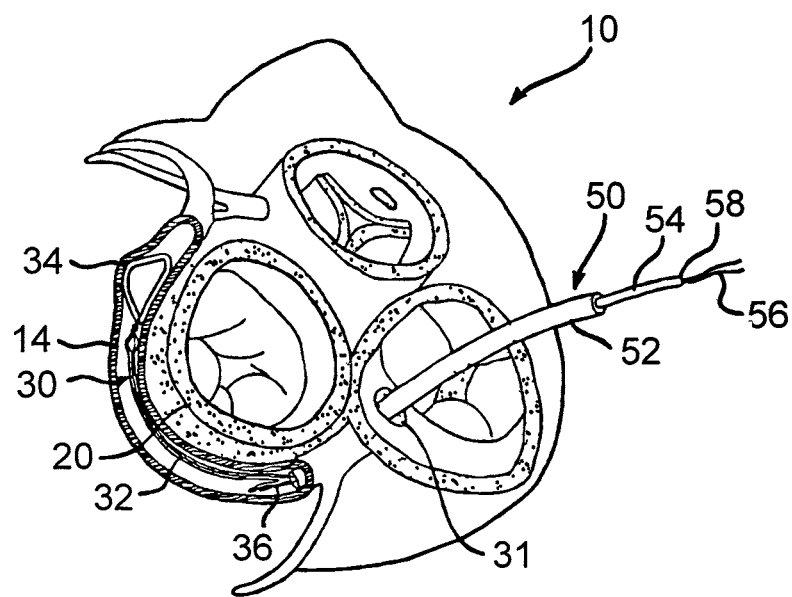
FIG. 2 shows a tissue shaping device and system according to one embodiment of the invention deployed within a coronary sinus of the heart.

FIG. 2 shows a tissue shaping device 30 deployed in the coronary sinus 14 of the heart 10 adjacent the mitral valve annulus 20 for reshaping the mitral valve annulus, the target tissue for this use of the device. Also shown in FIG. 2 is a deployment system 50 that deploys the device 30 in the coronary sinus 14. The device 30 takes the form of an elongated body 32 which includes a distal anchor 34 and a proximal anchor 36.

Anchors 34 and 36 are shown in FIG. 2 in their deployed configuration. As described below, upon deployment of the device 30 in the coronary sinus, the distal anchor 34 is transitioned from a first configuration to a locked second configuration. In the process, it is expanded outwardly to anchor the device in the coronary sinus against both bidirectional longitudinal and rotational movement. The proximal anchor in this embodiment, however, is configured to permit proximal movement when deployed. This allows the device 30 to be tightened within the coronary sinus by proximal pulling of the anchor 36 after the distal anchor 34 is deployed. The device 30 may be formed from Nitinol or stainless steel, for example.

The deployment system 50 illustrated in FIG. 2 includes an elongated catheter 52, an elongated pusher 54, and a tether 56. In deploying the device 30, the tether 56 is first looped about the proximal anchor 36 of the device 30 as illustrated and the device is then loaded into the catheter 50. The tether 56 is then threaded through an internal lumen 58 of the pusher 54 and looped around the proximal anchor 36 of the device 30 as illustrated. The pusher 54 is then advanced along the tether 56 for engaging the device 30 and pushing the device distally down the catheter to a predetermined position at the distal end of the catheter 50. The catheter with the device 30 loaded therein is then fed into the heart and through the coronary sinus ostium 31 into the coronary sinus to place the catheter in a position such that the device 30 is adjacent the mitral valve annulus 20. Thereafter, the device is maintained in a stationary position by the pusher 54 as the catheter 50 is partially withdrawn to expose the distal anchor 34.

Once the distal anchor is exposed, it is deployed by the catheter in a manner to be described more particularly with respect to FIGS. 3-6. Once the distal anchor 34 is deployed, the catheter 50 is then retracted proximally of the proximal anchor 36. This exposes the proximal anchor 36 and permits the proximal anchor to self deploy. Once the proximal anchor is deployed, the tether 56 is pulled proximally to move the proximal anchor 36 in a proximal direction for tightening the device within the coronary sinus and to an extent which results in the desired effect on the geometry of the mitral valve annulus 20. During this adjustment process, mitral regurgitation may be monitored and the device adjusted for optimal results. When the device 30 is in its final position within the coronary sinus 14, the pusher 54 and catheter 50 may be removed from the heart. The tether 56 may be permitted to remain in the heart during an acute phase to ascertain the effectiveness of the device 30. Should further adjustment of the device be necessary, the tether 56 may then be used as a guide for guiding the introduction of the catheter 50 back into the heart.

Figure 3:
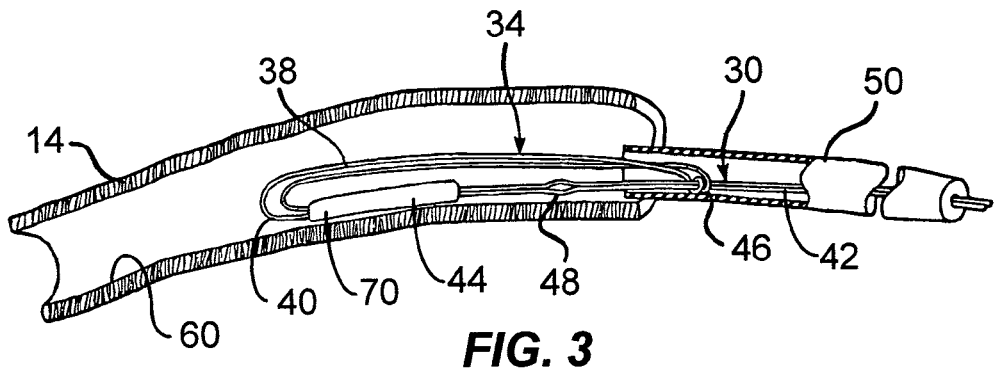
FIG. 3 is a side view with portions cut away illustrating a first step in deploying the anchor of the device shown in FIG. 2.

FIGS. 3-6 illustrate the manner in which the distal anchor 34 may be deployed in the coronary sinus 14 for anchoring the device 30. In each of FIGS. 3-6 a portion of the coronary sinus has been removed and the pusher has not been illustrated so as to not unduly complicate the figures. FIG. 3 shows the catheter 50 disposed within the coronary sinus 14 with most of the device 30 and part of distal anchor within the catheter 50. To that end, the catheter includes a lumen 60 which is dimensioned to receive the device 30 and the distal anchor 34 when the distal anchor 34 is in a first configuration. The distal anchor 34 includes an anchoring portion 38 connected to a base portion 44 at distal and proximal points 40 and 46. In this embodiment, base portion 44 includes a crimp 70 holding the distal end of anchoring portion 38 as well as the distal portion of a connector 42. The proximal connection point 46 of anchoring portion 38 is formed as a loop extending around connector 42 to serve as an element of the anchor's lock, as explained below. The wire forming anchoring portion 38 is bent into a FIG. 8 configuration whose height may be changed and locked by moving the proximal connection point 46 distally or proximally, as described below.

A lock bump 48 is formed in connector 42 to form another portion of the anchor's lock. The shape of lock bump 48 may be changed elastically to permit loop 46 slide to slide over it in a proximal or distal direction. When the loop 46 is located distally of lock bump 48, it will be held by the enlarged portion 48 for locking the device in the second configuration.

Figure 4:
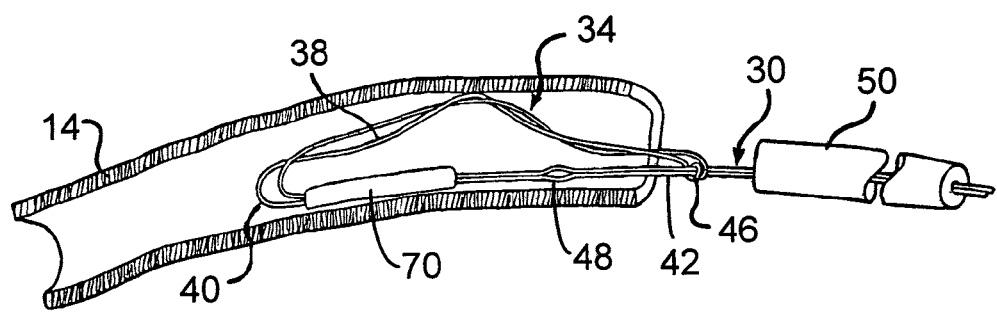
FIG. 4 is a side view similar to FIG. 3 illustrating a further step in the deployment of the anchor of the device shown in FIG. 2.

FIG. 4 illustrates the anchor 34 after the catheter 50 has been moved proximal to the anchor 34. More specifically, it will be noted that the distal end of the catheter 50 is now proximal to the loop 46 at the proximal end of the anchor 34. The shape memory of the anchor has caused the anchor to expand and is now partially transitioned from the first configuration of FIG. 3 to the second and final configuration to be described with reference to FIG. 6.

Figure 5:
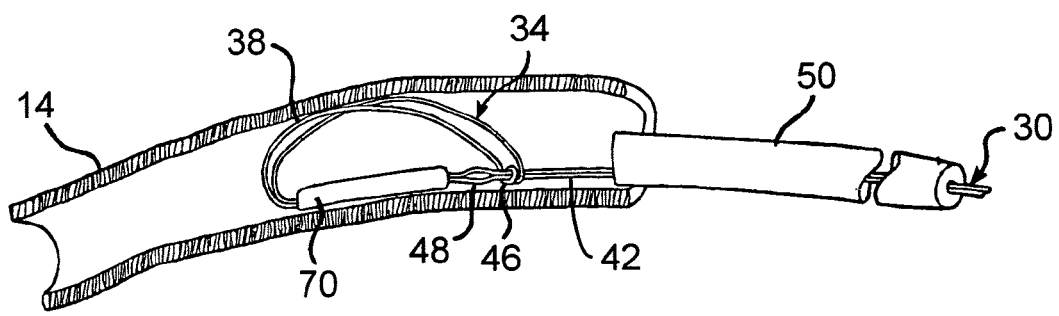
FIG. 5 is a side view similar to FIG. 3 illustrating a further step in the deployment of the device shown in FIG. 2 showing the anchor is an expanded but not yet locked configuration.
Figure 6:
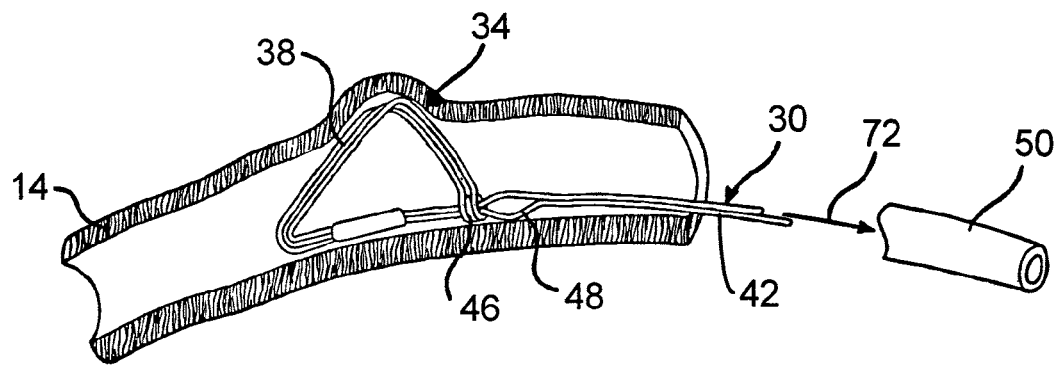
FIG. 6 is a side view similar to FIG. 3 illustrating a further step in the deployment of the device shown in FIG. 2 showing the anchor is an expanded locked configuration.

FIGS. 5 and 6 further illustrate anchor 34 being moved from the first configuration to the second configuration by using catheter 50 as a tool to adjust and lock the anchor's height.

FIG. 5 shows anchor 34 prior to locking. Distal end of catheter 50 may be used to apply an actuation force to push distally on an interface portion at the proximal end of the anchor 34 while the tether (not shown) holds the device 30 against distal movement, thereby expanding anchor 34 and increasing its anchor height.

As the catheter 50 is moved distally, it forces the loop 46 of the anchor 34 over the lock bump 48 to lock anchor 34 in the expanded second configuration. This provides for anchoring within the coronary sinus of the device 30 against both bidirectional longitudinal and rotational movement. Once the anchor 34 is deployed as illustrated in FIG. 6, the catheter 50 may then be moved proximally and/or removed as indicated by the arrow 72.

One of the many features of the anchor of the instant invention is that it may be moved within or removed from the body lumen in which it is deployed. More specifically, and making reference to FIG. 6, the anchor 34 may be removed by grabbing the proximal side of anchoring portion 38 and pulling the loop 46 proximally over lock bump 48 to collapse the anchor to enable removal of the device within the catheter 50.

Further details of the construction and operation of the device described with respect to FIGS. 2-6 may be found in U.S. application Ser. No. 09/142,637.

Figure 7:
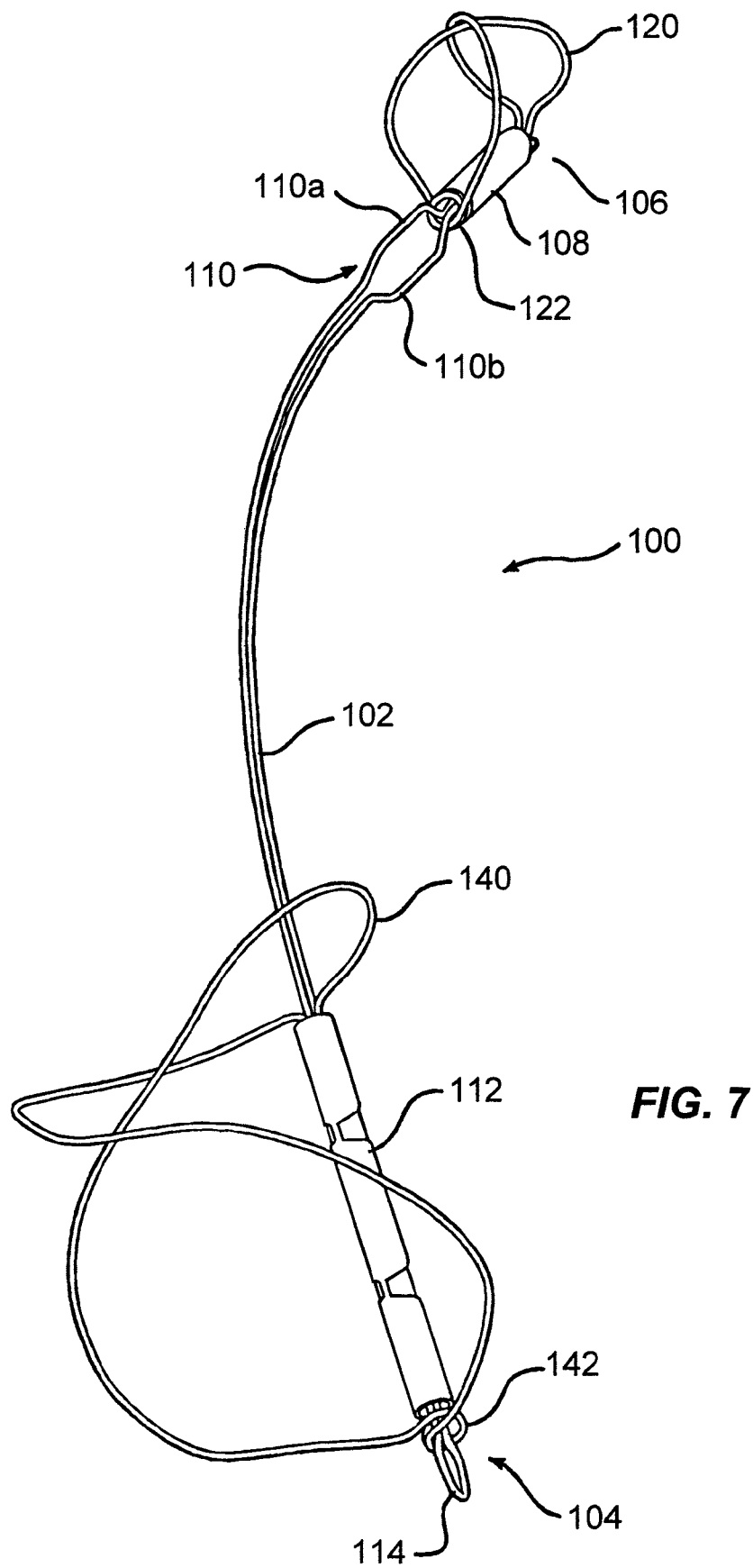
FIG. 7 is a perspective view of a tissue shaping device according to another embodiment of the invention.

FIG. 7 shows an embodiment of a tissue shaping device 100 in which both distal anchor 120 and proximal anchor 140 are expandable and lockable. Device 100 includes a connector such as support wire 102 having a proximal end 104 and a distal end 106. Connector 102 is made of a biocompatible material such as stainless steel or a shape memory material such as nitinol wire.

In this embodiment, connector 102 comprises a double length of nitinol wire that has both ends positioned within a distal crimp tube 108. To form the connector 102, the wire extends distally from the crimp tube 108 where it is bent to form a distal stop loop having a diameter that is larger than the lumens within the distal crimp tube 108. After forming the distal stop loop, the wire returns proximally through the crimp tube 108 towards the proximal end of the device 100. Proximal to the proximal end of the crimp tube 108 is a distal lock bump 110 that is formed by the connector bending away from the longitudinal axis of the device 102 and then being bent parallel to the longitudinal axis of the support before being bent again towards the longitudinal axis of the support. Therefore, the bends in the connector form a half 110a of the distal lock bump that is used to secure the distal anchor in the manner described below. From the distal lock bump 110, the wire continues proximally through a proximal crimp tube 112. On exiting the proximal end of the proximal crimp tube 112, the wire is bent to form an arrowhead-shaped proximal lock bump 114. The wire of the connector 102 then returns distally through the proximal crimp tube 112 to a position just proximal to the proximal end of the distal crimp tube 108 wherein the wire is bent to form a second half 110b of the distal lock bump 110.

At the distal end of connector 102 is a distal anchor 120 that is formed of a flexible wire such as nitinol or some other shape memory material. The wire forming the distal anchor has one end positioned within the distal crimp tube 108. After exiting the distal end of the crimp tube 108, the wire forms a figure eight configuration whereby it bends upward and radially outward from the longitudinal axis of the crimp tube 108. The wire then bends back proximally and crosses the longitudinal axis of the crimp tube 108 to form one leg of the figure eight. The wire is then bent to form a double loop eyelet or loop 122 around the longitudinal axis of the connector 102 before extending radially outwards and distally back over the longitudinal axis of the crimp tube 108 to form the other leg of the figure eight. Finally, the wire is bent proximally into the distal end of the crimp tube 108 to complete the distal anchor 120.

As in the embodiment described above with respect to FIGS. 2-6, the distal anchor is expanded moving the delivery catheter distally to engage the proximal portion of anchor 120 and double eyelet 122 and move it from a position that is proximal to the distal lock bump 110 on the connector to a position that is distal to the distal lock bump 110. The bent-out portions 110a and 110b of connector 102 are spaced wider than the width of double eyelet 122 and provide camming surfaces for the locking action. Distal movement of eyelet 122 pushes these camming surfaces inward to permit eyelet 122 to pass distally of the lock bump 110, then return to their original spacing to keep eyelet 122 in the locked position.

At the proximal end of the device is a proximal anchor 140 that is preferably formed of a biocompatible, elastic wire such as stainless steel or a shape memory material such as nitinol. Proximal anchor 140 is made of a single length of wire having a first end positioned within a proximal crimp tube 112. The wire extends distally from the crimp tube 112 and bends radially outward and away from the longitudinal axis of the crimp tube 112 before being bent proximally and crossing the longitudinal axis of the crimp tube 112 in order to form a first leg of a figure eight configuration. The wire then is bent to form a double eyelet or loop 142 around the longitudinal axis of the connector 102 wherein the eyelet 142 has a diameter that allows it to be forced over the proximal lock 114. After forming the eyelet 142, the wire extends outwardly and away from the longitudinal axis of the crimp tube 112 before being bent distally over and across the longitudinal axis of the crimp tube 112 to form the second leg of a figure eight. Finally, the wire is bent proximally and extends into the distal end of the crimp tube 112.

Like the distal anchor, the proximal anchor is expanded and locked by advancing the delivery catheter distally to engage the proximal side of anchor 140 to move the double eyelet 142 from a position that is proximal to the proximal lock bump 114 to a position that is distal to the proximal lock bump 114 in the manner described above with respect to FIGS. 2-6. As can be seen in FIG. 7, the proximal lock bump 114 has an arrowhead shape whereby the proximal end of the lock is bent away from the longitudinal axis of the connector at an angle that is less steep than the distal end of the proximal lock bump. The less steep section makes it easier to advance the eyelet 142 over the lock bump 114 in the distal direction than to retrieve the eyelet 142 over the lock bump in the proximal direction. Distal movement of eyelet 142 cams the less steep proximal surfaces inward to permit eyelet 142 to pass distally of the lock bump 114, then return to their original spacing to keep eyelet 142 in the locked position. Further details of the construction and operation of device 100 may be found in U.S. application Ser. No. 10/429,172.

Figure 8:
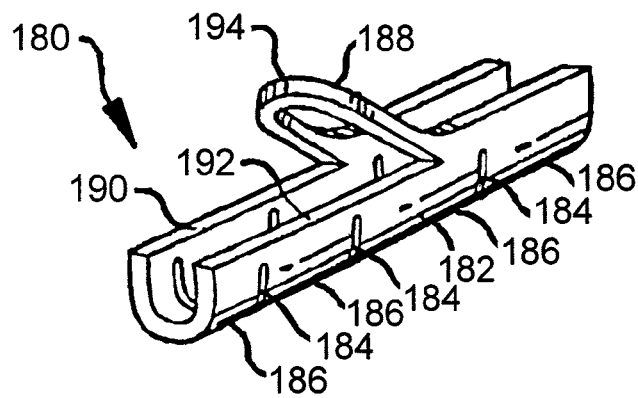
FIG. 8 is a perspective view of a tissue shaping device according to yet another embodiment of the invention.

FIG. 8 is a perspective view a focused compression mitral valve device 180, also known as a focal deflector. The device has an elongated semi-tubular base 182 having cut-out portions 184 to allow bending of the base 182. Between the cut-out portions 184 are semi-cylindrical surfaces 186 arranged to continuously contact the pericardial wall of the coronary sinus when the device 180 is implanted in the coronary sinus to distribute the applied force.

The device 180 further includes a force applying member 188 which extends from opposed sidewalls 190 and 192 intermediate the ends of the base 182. The member 188 has an end 194 for engaging a discrete portion of the atrial wall of the coronary sinus to apply the applied force to a discrete portion of the mitral valve annulus to reshape the mitral valve annulus. Further details of device 180 may be found in U.S. application Ser. No. 10/003,910.

Figure 9:
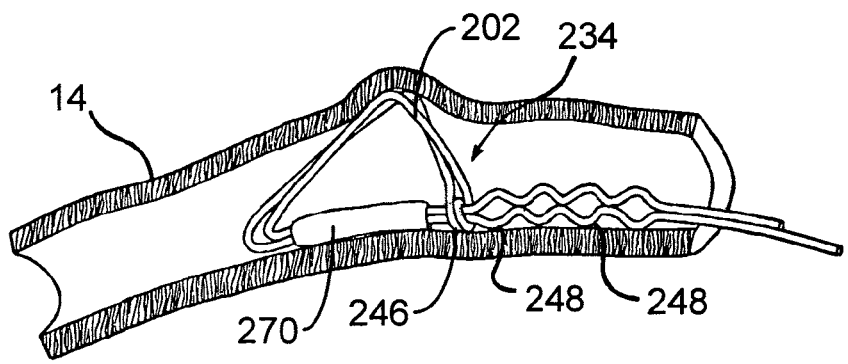
FIG. 9 is a side view of an adjustable height anchor of a tissue shaping device according to still another embodiment of the invention.

FIG. 9 shows an anchor design that may be used in place of anchors 34 or 36 of device 30 in FIGS. 2-6, anchors 120 or 140 of device 100 in FIG. 7, or focal deflector 180 in FIG. 8. As in the devices shown in FIGS. 2-7, adjustable height anchor 234 is formed from a wire 202 bent into a FIG. 8 configuration. Wire 202 is held by a base, such as crimp tube 270. Wire 202 has an eyelet 246 on its proximal side that cooperates with a series of lock bumps 248. To expand the anchor, an actuation tool such as the delivery catheter (not shown) applies a distally directed force on anchor 234 to move eyelet 246 distally over one or more lock bumps. The lock bumps change shape to capture and lock the anchor, as described above. The series of lock bumps register the anchor in discrete and predetermined anchor heights so that the anchor height and the anchoring force can be adjusted. Likewise, a proximally directed force on the anchor will move eyelet 246 proximally over the lock bumps to decrease anchor height and the anchoring force.

Figure 10:
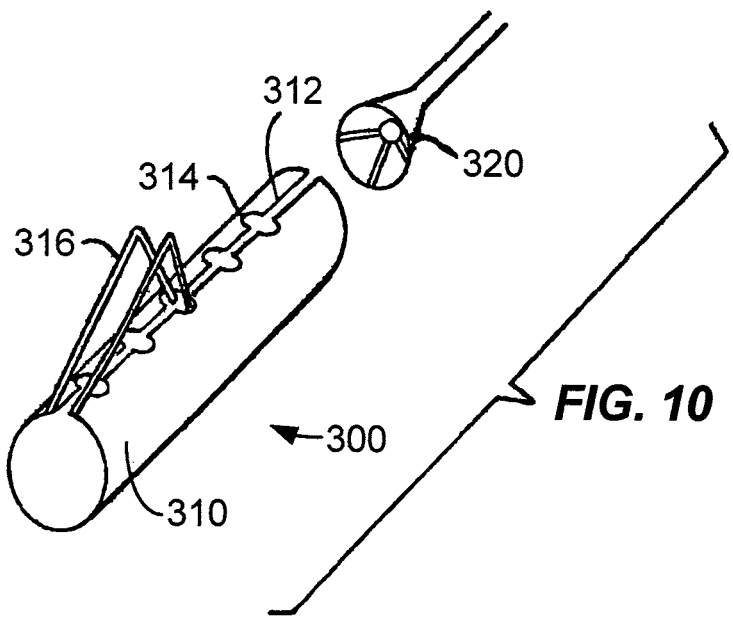
FIG. 10 is a perspective view of a tissue shaping system according to yet another embodiment of the invention.
Figure 11:
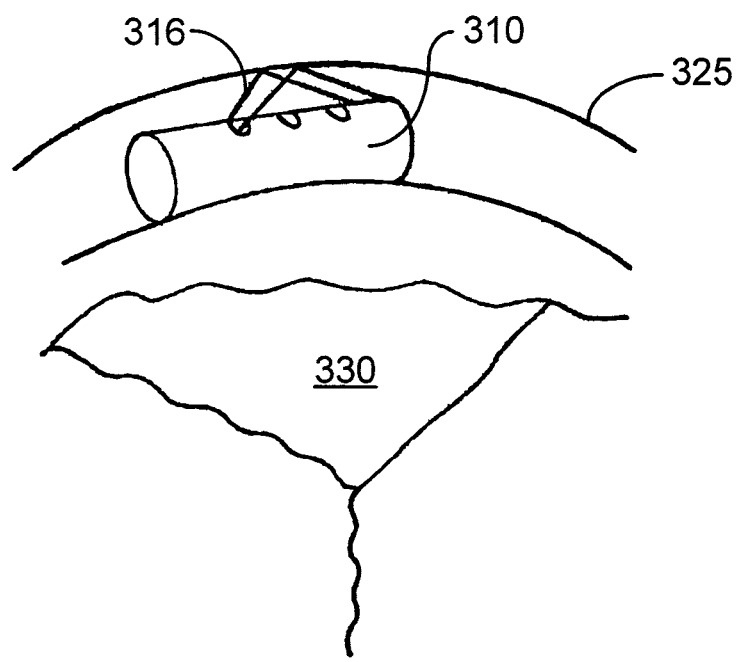
FIG. 11 is a side view of the tissue shaping device of claim 10 as deployed in a coronary sinus.

FIGS. 10 and 11 show yet another embodiment of a tissue shaping device with an adjustable height anchor, such as an anchor used as a focal tissue deflector. Anchor 300 includes a cylindrical tube 310 having a central slot 312 that extends along a length of the tube and a series of opposing slots 314 that extend in a direction that is perpendicular to the length of the slot 312. Anchor 300 also has anchoring portion made up of a pair of legs 316 each having a fixed end secured to the tube 310 and a free end that is positioned in one of the series of opposing slots 314. Preferably, the legs 316 are made of a superelastic material such as Nitinol or other biocompatible elastic material. By selecting a different slot for the free ends of the legs, the height of the legs can be readily adjusted.

To adjust the height of anchor 300, a tool 320 having a funnel or other shaped end is inserted into the tube 310 to engage the free ends of the legs and move them to the center slot 312 to allow them to be placed in another pair of opposing slots 314. Preferably, the legs 316 are biased radially outward such that when positioned adjacent to a slot 314 and released, they will be biased towards the ends of the slots 314. The series of slots register the anchor in discrete and predetermined anchor heights so that the anchor height and the anchoring force can be adjusted.

FIG. 11 shows the anchor of FIG. 10 within a vessel 325, such as the coronary sinus. The legs 316 engage a vessel wall 332 and press the tube 310 on the side of the vessel wall adjacent tissue to be reshaped. In the example shown, the anatomy comprises a mitral valve 330 that is urged closed by the presence of the tissue shaping device in the vessel.

This anchor embodiment could also be used as the proximal or distal anchor of a tissue deflecting device, such as the devices described above. The anchor's variable height permits the user to provide the appropriate minimum amount of expansive force to securely anchor the tissue deflecting device, thereby minimizing any effects of over-expansion of an anchor.

Figure 12:
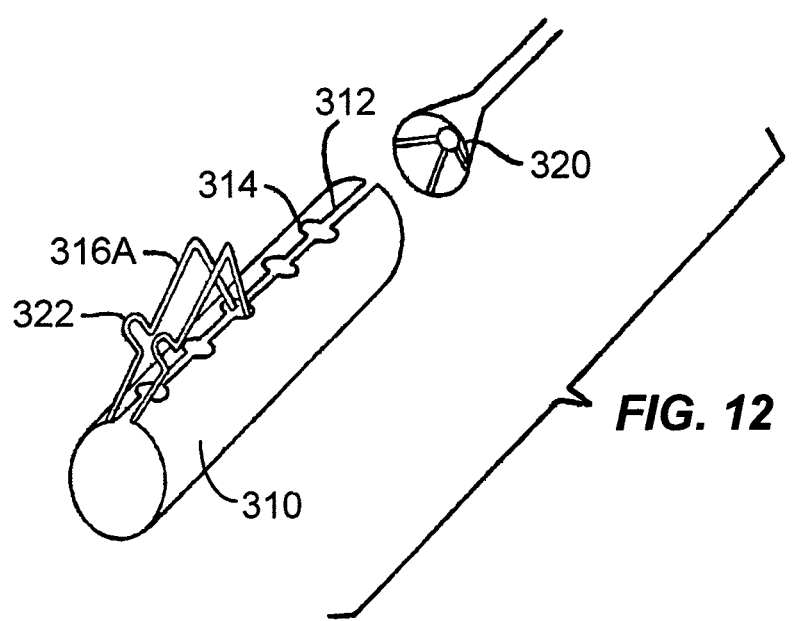
FIG. 12 is a perspective view of a tissue shaping system according to yet another embodiment of the invention.

An alternative embodiment is shown in FIG. 12, in which the legs 316A of the anchor are provided with barbs 322 to facilitate anchoring. This geometry would also facilitate collapse of the legs by tool 320 by placing a tensile load on tool 320. Other geometries for the legs are possible, of course, without departing from the invention.

What is claimed is:

1. A tissue shaping device adapted to reshape target tissue, comprising:
    an expandable anchor and a connector element extending from the expandable anchor;
    a delivery catheter in which the expandable anchor and the connector are delivered to a lumen within a patient, wherein the expandable anchor has a collapsed delivery configuration within the delivery catheter; and
    a lock that is adapted to lock the expandable anchor in one of a plurality of locked configurations within a lumen, wherein the lock comprises a first lock element and a second lock element which are movable relative to one another to lock the first lock element and the second lock element in a locked configuration to thereby lock the expandable anchor in one of the plurality of locked configurations.

2. The device of claim 1 wherein the plurality of locked configurations are locked and expanded configurations.

3. The device of claim 1 wherein the lock is further adapted to lock the expandable anchor in a plurality of locked configurations in the absence of bodily forces acting on the expandable anchor.

4. The device of claim 1 wherein the expandable anchor comprises a bent wire when the expandable anchor is in each of the plurality of locked configurations.

5. The device of claim 4 wherein in each of the plurality of locked configurations the bent wire has a configuration which is different from a configuration of each of the other plurality of locked configurations.

6. The device of claim 1 wherein the expandable anchor comprises the first lock element and the connector element comprises the second lock element.

7. The device of claim 6 wherein the second lock element comprises a plurality of discrete locking features to lock the expandable anchor in the plurality of locked configurations.

8. The device of claim 1 wherein the delivery catheter engages the expandable anchor to lock the expandable anchor in one of the plurality of locked configurations.

9. The device of claim 8 wherein the lock comprises a first lock element and a second lock element, and wherein the delivery catheter engages the expandable anchor to move the first lock element relative to the second lock element to thereby lock the expandable anchor in one of the plurality of locked configurations.

10. The device of claim 9 wherein the second lock element comprises a plurality of discrete locking features to lock the expandable anchor in one of the plurality of locked configurations.

11. The device of claim 10 wherein the anchor comprises the first lock element and the connector element comprises the second lock element.

12. The device of claim 1 wherein the device further comprises a second expandable anchor, wherein the connector element connects the first and second expandable anchors.

13. The device of claim 12 further comprising a second lock that is adapted to lock the second expandable anchor in one of a plurality of locked configurations.

14. The device of claim 12 further comprising a second lock that is adapted to lock the second expandable anchor in only one locked configuration.

15. A method of reshaping target tissue adjacent to a lumen, comprising:

delivering an expandable anchor and a connector element extending from the expandable anchor within a delivery catheter to a target location within a lumen, wherein the expandable anchor is delivered in a collapsed delivery configuration;
    deploying the expandable anchor from the delivery catheter;
    locking the expandable anchor in one of a plurality of locked configurations in the lumen, wherein the locking step comprises moving a first lock element relative to a second lock element to engage the first and second lock element in a locked configuration to thereby lock the expandable anchor in one of the plurality of locked configurations.

16. The method of claim 15 wherein deploying the expandable anchor from the delivery catheter comprises allowing the expandable anchor to expand from the delivery catheter.

17. The method of claim 15 wherein the expandable anchor comprises the first lock element and the connector element comprises the second lock element.

18. The method of claim 17 wherein the second lock element comprises a plurality of discrete locking features such that moving the first lock element relative to the second lock element comprises moving the first lock element relative to the plurality of discrete locking features.

19. The method of claim 15 wherein locking the expandable anchor in one of a plurality of locked configurations comprises engaging the expandable anchor with the delivery catheter to move a first locking element with respect to a second locking element to thereby engage the first and second locking elements in a locked configuration to thereby lock the expandable anchor in one of the plurality of locked configurations.

20. The method of claim 19 wherein engaging the expandable anchor with the delivery catheter comprises applying a distally directed force on the expandable anchor with the delivery catheter.

21. The method of claim 15 further comprising adjusting the configuration of the expandable anchor after the deploying step and before the locking step.

22. The method of claim 21 wherein adjusting step comprises applying an actuating force on the expandable anchor with the delivery catheter.

23. A tissue shaping device adapted to reshape target tissue, comprising:
    a radially expandable anchor and a connector element extending from the expandable anchor;
    a delivery catheter in which the radially expandable anchor and the connector are delivered to a lumen within a patient, wherein the radially expandable anchor has a radially collapsed delivery configuration within the delivery catheter; and
    a lock that is adapted to lock the radially expandable anchor in one of a plurality of locked configurations within a lumen.

24. The device of claim 23 wherein the plurality of locked configurations are locked and radially expanded configurations.

25. The device of claim 23 wherein the lock is further adapted to lock the radially expandable anchor in a plurality of locked configurations in the absence of bodily forces acting on the expandable anchor.

26. The device of claim 23 wherein the radially expandable anchor comprises the first lock element and the connector element comprises the second lock element.

27. The device of claim 26 wherein the second lock element comprises a plurality of discrete locking features to lock the expandable anchor in the plurality of locked configurations.

28. The device of claim 23 wherein the device further comprises a second expandable anchor, wherein the connector element connects the first and second expandable anchors.

* * * * *